United States Patent [19]
Niizawa et al.

[11] Patent Number: 5,381,227
[45] Date of Patent: Jan. 10, 1995

[54] STANDARD MATERIALS AND METHODS FOR INSTRUMENTAL MEASUREMENT FOR ASTM COLOR OF PETROLEUM PRODUCTS USING SAID STANDARD MATERIALS

[75] Inventors: Akihiko Niizawa; Masahiro Yamaguchi, both of Yokohama, Japan

[73] Assignees: Nippon Petroleum Refining Co., Ltd.; The Japan Petroleum Institute, Tokyo, Japan

[21] Appl. No.: 32,881

[22] Filed: Mar. 18, 1993

[30] Foreign Application Priority Data

Mar. 31, 1992 [JP] Japan .................................. 4-103879

[51] Int. Cl.⁶ .................................................. G01J 1/02
[52] U.S. Cl. .......................................... 356/243; 356/70
[58] Field of Search ................................. 356/243, 70

[56] References Cited
U.S. PATENT DOCUMENTS 5,139,330 8/1992 Niizawa et al. ...................... 356/70

*Primary Examiner*—Rolf Hille
*Assistant Examiner*—Roy Potter
*Attorney, Agent, or Firm*—Bucknam and Archer

[57] ABSTRACT

A set of standard materials, which comprises at least two kinds of standard materials, for calibration of a photoelectric colorimeter used for the instrumental measurement of petroleum products for their ASTM color, comprising at least two kinds of standard materials each of which is a mixed solution having a color corresponding to an ASTM color and comprises (a) at least five members selected from the group consisting of seven specific colorants such as 3-methyl-1-phenyl-4-(phenylazo)-pyrazol-5-ol, 1-(phenylazo)-2-naphthalenol and 1-[[4-[(dimethylphenyl)azo]dimethylphenyl]azo]-2-naphthalenol, (b) 1-phenyl-1-xylylethane as a solvent for said colorants, and (c) dodecane as a diluent; and a method for instrumental measurement of petroleum products for their ASTM color by a photoelectric colorimeter, which comprises calibrating the photoelectric colorimeter by the use of said at least two kinds of standard materials.

2 Claims, 1 Drawing Sheet

STANDARD MATERIALS AND METHODS FOR INSTRUMENTAL MEASUREMENT FOR ASTM COLOR OF PETROLEUM PRODUCTS USING SAID STANDARD MATERIALS

BACKGROUND OF THE INVENTION

1. Field of the Invention

The present invention relates to standard (reference) materials for calibration of a photoelectric colorimeter (color and color-difference meter) which is used for instrumental measurement for ASTM color, said measurement being colorimetry of petroleum products such as various lubricating oils. petrolatum and microcrystalline wax. The present invention also relates to a method for Instrumental measurement for ASTM color of a petroleum product using said standard materials (standard samples).

2. Prior Art

There are two testing methods for colorimetry of petroleum products, one being a method for measuring ASTM color of petroleum products and the other a method for measuring Saybolt color thereof as prescribed in JIS K 2580.

Of these, the method for measuring ASTM color is applied to various lubricating oils and petrolatum, etc. and will indicate the color of a test material in terms of a symbol or a value ranging from 0.5 (light) to 8.0 (dark) obtained by comparing the color of the test material with that of a standard (reference) colored grass (glass color standard) by generally using an ASTM chromometer.

It is noted that the ASTM color of a material is expressed as a symbol or a value (any one of 0.5 to 8.0 in accordance with JIS K 2580) which is assigned to a standard colored glass whose color corresponds to the color of the material.

The standard colored glass used in the above method is prescribed to have its color dispersion limited as indicated in the XYZ colorimetric system in accordance with JIS Z 8722, the luminous transmittances using the CIE standard Illuminant C and the chromaticity coordinates based on the RGB color system.

However, in cases where the ASTM color of a material is measured by the use of the ASTM chromometer, the ASTM color so found is Judged by human vision and the results expressed by said measurement are not quantitative {when the thus found color of a test material used is between those (for example, 4.0 and 4.5 in ASTM color) of two different standard colored glasses, it is expressed as L 4.5 (this 4.5 is a symbol for the standard colored glass having a darker color), while when the color of the test material is darker than 8.0 in ASTM color then It is expressed as D 8.0} and, therefore, personal differences in judgment are apt to be made and time measurers practically worry about the judgement. This tendency is particularly remarkable when the color of the test material is dense or dark.

Accordingly, even in such a colorimetry as above, automatization of judgment of color without resort to visual Judgment is eagerly desired at the present time.

In view of the above, the present inventors attempted to investigate whether or not a commercially available photoelectric colorimeter (measuring instrument) can be used for measuring a test material for its ASTM color.

A photoelectric colorimeter used must be one which will produce a favorable correlation with the testing method as prescribed in JIS K 2580 in the entire region of ASTM color ranging from 0.5 to 8.0. Furthermore, there is desired a universal method for testing a material, especially a liquid, for its color.

For the perception of color with human eyes under natural light, the quantities of stimuli due to three primary colors of lights which are red, green and blue lights, are important. In measuring a color with an optical instrument, a light emitted from a light source is used instead of the natural light and what is important is not the quantities of stimuli but tristimulus values.

Accordingly, it is desirable that a method testing a test material for ASTM color be a universal method, whose performance is close to the perception of color with human eyes, based on the tristimulus values by an optical instrument and that the expression of the results of measurement be a quantitative expression without the use of L OF D color expression. Therefore, it is desirable to adopt a testing method based on methods for measuring a material (methods for measurement of reflecting or transmitting objects for their color) which are recommended by Commission Internatlonale de l'Eclairage (hereinafter abbreviated as "CIE") and prescribed in JIS Z 8722 and also to adopt a method for quantitatively expressing measured results based on the color expression method using the XYZ colorimetric system prescribed in JIS Z 8701.

In measuring a sample for its color by a photoelectric colorimeter, it is necessary to express the measured value of the sample obtained by a commercially available photoelectric colorimeter in terms of the ASTM color. Therefore, it is necessary to find the correlation between the tristimulus value and ASTM color.

Comparing the sum ($\Sigma D$) of optical densities based on the XYZ colorimetric system of standard colored glasses with the ASTM color of the same, the present inventors have found a correlation therebetween as represented by the following correlation formula:

$$A = \alpha \Sigma D + \beta$$

wherein A is ASTM color, $\Sigma D$ is the sum of optical densities (DX+DY+DZ), and $\alpha$ and $\beta$ are each a constant for calibration of instrumental errors.

Therefore, the measured value of the ASTM color is obtained by processing the measured X, Y and Z values in the operation-display section of the measuring instrument on the basis of said correlation formula.

As the above $\Sigma D$ value varies with an instrumental error depending on an instrument used, it cannot always be constant even for the same material. It is necessary, therefore, to prepare at least two kinds of standard liquid materials for finding at least two ASTM colors to calibrate each instrument (photoelectric colorimeter) with the standard liquid materials.

Such standard materials are required to be low volatile, highly resistant to oxidation, low degradable, for example low oxidizable, with the elapse of time and satisfactory in color stability.

SUMMARY OF THE INVENTION

The present invention has been made in view of the above facts, and an object thereof is to provide a set of standard materials to be used for measuring a test material for its ASTM color by the use of a photoelectric colorimeter (color and color-difference meter) and another object is to provide an instrumental measuring method using said standard materials.

In attempts to achieve the above objects, the present inventors made intensive studies and found that mixed solutions of specific mixed colorants (dyestuffs) suited for such objects as above and specific solvents coincide in color with standard colored glasses to be used in ASTM colorimetry and they are fully effective as standard materials.

In one aspect of the present invention, it resides in a set of standard materials comprising at least two kinds of standard materials for calibration of a photoelectric colorimeter used for instrumentally measuring petroleum products for their ASTM color. A set of standard materials comprises at least two kinds of standard materials and said at least two kinds of standard materials are each a mixed solution whose color corresponds to a predetermined ASTM color. Said mixed solutions are respectively prepared by mixing together (a) at least five colorants selected from the group consisting of (i) 3-methyl-1-phenyl-4-(phenylazo)-pyrazol-5-ol, (ii) 1-(phenylazo)-2-naphthalenol, (iii) 1-[[4-[(dimethylphenyl)azo]dimethylphenyl]azo]-2-naphthalenol, (iv) 1,5(or 1,8)-bis[(4-methylphenyl)amino]-9,10-anthracenedione, (v) 1-hydroxy4-[(4-methylphenyl)amino]-9,10-anthracenedione, (vi) 1,4-bis(butylamino)-9,10-anthracenedione and (vii) 1,4bis[(4-butylphenyl)amino]-5,8-dihydroxy-9,10-anthracenedione.

(b) 1-phenyl-1-xylylethane as a solvent for said colorants, and (c) dodecane as a diluent for the resulting solution.

In another aspect of the present invention, it resides in a method for instrumental measurement of petroleum products for their ASTM color by the use of a photoelectric colorimeter, which comprises calibrating the photoelectric colorimeter by using said at least two kinds of standard materials.

The present Invention will be explained hereunder in more detail.

Each of the colorants to be used in the present invention has the following chemical structure:

(i) 3-methyl-1-phenyl-4-(phenylazo)-pyrazol-5-ol

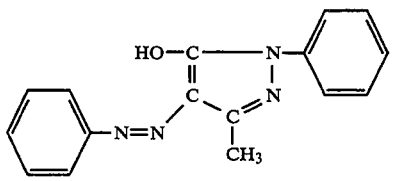

(CAS No. 4314-14-1)
Color index (CI): Solvent Yellow 16
Example: Oil Yellow 5GS Extra (tradename)

(ii) 1-(phenylazo)-2-naphthalenol

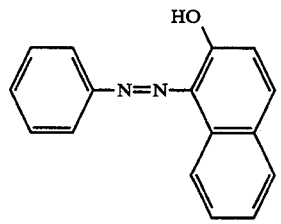

(CAS No. 842-07-9)
Color index (CI): Solvent Yellow 14
Example: Oil Orange Extra (tradename)

(iii) 1-[[4-[(dimethylphenyl)azo]dimethylphenyl]azo]-2-naphthalenol

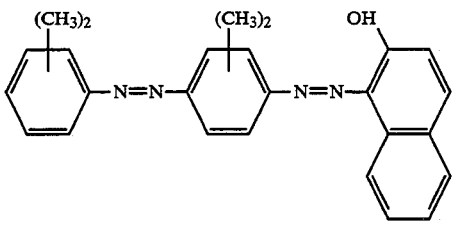

CAS No. 1320-06-5)
Color index (CI): Solvent Viloet 14
Example: Oil Red 5B Special (tradename)

(iv) 1,5(or 1,8)-bis[(4-methylphenyl)amino]-9,10-anthracenedione

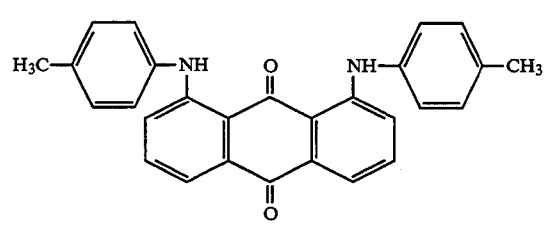

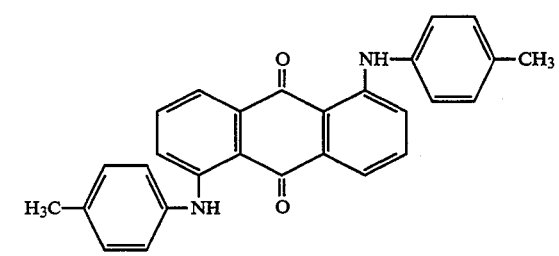

(CAS No. 8005-40-1)
Color index (CI): Solvent Viloet 14
Example: Oil Violet 3R (tradename)

(v) 1-hydroxy-4-[(4-methylphenyl)amino]-9,10-anthracenedione

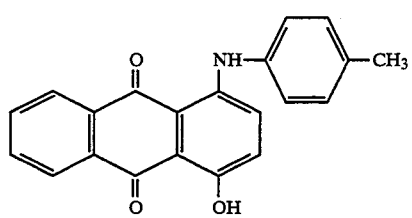

(CAS No. 81-48-1)
Color index (CI): Solvent Viloet 13
Example: Oil Violet B-2R (tradename)

(vi) 1,4-bis(butylamino)-9,10-anthracenedione

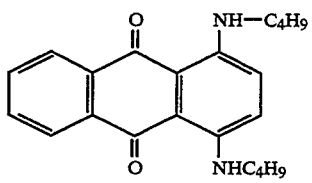

(CAS No. 17354-14-2)
Color index (CI): Solvent Blue 35
Example: Oil Blue SB (tradename)
(vii) 1,4-bis[(4-butylphenyl)amino]-5,8-dihydroxy-9,10-anthracenedione

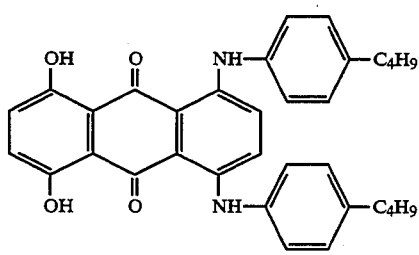

CAS No. 28198-05-2)
Color index (CI): Solvent Green 28
Example: Oil Green SG (tradename)

In the present invention, at least two, preferably at least three, more preferably at least four kinds of standard materials are prepared from a mixed colorant consisting of five to seven kinds of colorants selected from the colorants (i)-(vii), together with a specific solvent and a specific diluent. The mixing ratio of the colorants (i)-(vii) is preferably selected from the following mixing ratios (by volume) (1)-(4):

(1) (i)210:(ii)26:(iii)0:(iv)13:(v) 0:(vi)2:(vii)3,
(2) (i)200:(ii)29:(iii)7:(iv)6:(v) 4:(vi)2:(vii)4,
(3) (i)200:(ii)58:(iii)10:(iv)16:(v) 8:(vi)0:(vii)8, and
(4) (i)183:(ii)53:(iii)13:(iv)11:(v)16:(vi)1:(vii)3.

The use of not only a colorant mixture having a mixing ratio (1), (2), (3) or (4) but also the specific solvent and diluent, will produce a standard material whose color corresponds to an ASTM color 1, 3, 5 or 7.

In the preparation of standard materials of the present invention, 1-phenyl-1-xylylethane (hereinafter abbreviated to "PXE") and dodecane (hereinafter referred to as "n-$C_{12}$") are used as a solvent for the colorants and as a diluent, respectively as mentioned above.

A method for preparing a set of standard materials of the present invention will be concretely explained hereunder.

First, a predetermined amount of each of five to seven kinds of colorants selected from the colorants (i)-(vii) mentioned above is dissolved in PXE solvent to obtain a 1000 ppm(wt/vol %) dilute solution of the colorant. Next, the five to seven kinds of dilute solutions thus obtained are mixed together in predetermined mixing ratios (for example, the aforesaid mixing ratios (1)-(4)) to obtain at least two, for example four, kinds of mixed solutions. Subsequently, a predetermined amount of each of these mixed solutions is diluted with n-$C_{12}$ (for example, diluted to such an extent as specified in Table 1) to obtain a standard material whose color corresponds to a predetermined ASTM color. Thus there can be prepared a set of standard materials of the present invention comprising at least two kinds of standard materials whose colors correspond respectively to at least two different ASTM colors.

The instrumental measuring method of the present invention will be described hereunder.

First, one (having an ASTM color of 7.0 for example) of a set of standard materials of the present invention is measured for its ASTM color by a photoelectric colorimeter on the basis of the sum ($\Sigma D$) of optical densities of said standard material and a preliminarily obtained correlation formula. If the ASTM color found is 6.98, the photoelectric colorimeter will be calibrated so that it indicates an ASTM color of 7.0 by the use of the correction key at the operation-display section of the photoelectric colorimeter.

Subsequently, the photoelectric colorimeter is calibrated in turn by the use of another or other standard material(s) (having an ASTM color of 1.0 for example) in the same manner as mentioned above. Such calibration (correction) of the photoelectric colorimeter makes it possible to correctly measure a petroleum product for its ASTM color by the use of a photoelectric colorimeter. The above calibration of the photoelectric colorimeter should be carried out on at least two, preferably at least three, more preferably at least four, ASTM colors in the range of 0.5 to 8.0.

As described hereinbefore, the instrumental measurement of a petroleum product for its ASTM color can be carried out quantitatively and accurately by the use of the standard materials of the present invention.

DESCRIPTION OF THE PREFERRED EMBODIMENTS

Figure 1:
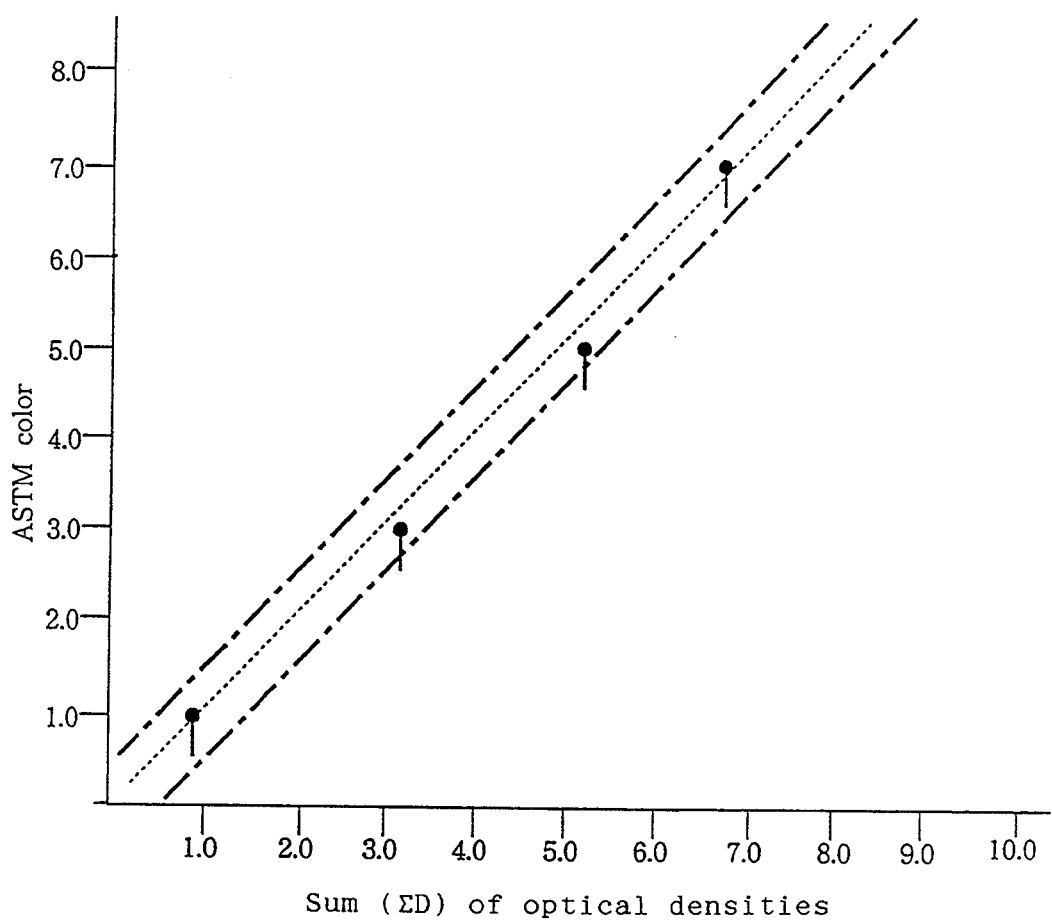
FIG. 1 is a graph showing the correlation between the sum ($\Sigma D$) of optical densities and the ASTM colors.

The present invention will be described in more detail by referring to the following Examples.

EXAMPLE 1

A predetermined amount of each of seven kinds of colorants, (i) 3-methyl-1-phenyl-4-(phenylazo)-pyrazol-5-ol, (ii) 1-(phenylazo)-2-naphthalenol, (iii) 1-[[4-[(dimethylphenyl)azo]dimethylphenyl]azo]-2-naphthalenol, (iv) 1,5(or 1,8)-bis[(4-methylphenyl)amino]-9,10-anthracenedione, (v) 1-hydroxy-4-[(4methylphenyl)amino]-9,10-anthracenedione, (vi) 1,4-bis(butylamino)-9,10-anthracenedione and (vii) 1,4-bis[(4-butylphenyl)amino]-5,8-dihydroxy-9,10-anthracenedione, was dissolved in 1-phenyl-1-xylylethane to obtain a 1000 ppm(wt/vol %) dilute solution thereof. Next, seven kinds of the dilute solutions thus obtained were mixed together in the mixing ratios by volume of:

(1(i)210:(ii)26:(iii)0:(iv)13:(v) 0:(vi)2:(vii)3,
(2) (i)200:(ii)29:(iii)7:(iv)6:(v) 4:(vi)2:(vii)4,
(3) (i)200:(ii)58:(iii)10:(iv)16:(v) 8:(vi)0:(vii)8, and
(4) (i)183:(ii)53:(iii)13:(iv)11:(v)16:(vi)1:(vii)3, to obtain four kinds of mixed solutions. Subsequently, a predetermined amount of each of the four kinds of mixed solutions was diluted with n-$C_{12}$ to such an extent as specified in Table 1 to prepare four kinds of standard materials whose colors correspond respectively to ASTM colors 1, 3, 5 and 7.

The sum ($\Sigma D$) of optical densities of each of these standard materials was measured by the use of a photoelectric colorimeter(Chroma meter CT-210 custom, produced by Minolta Camera Co., Ltd.) in which a sampling cell having a cell length of 33 mm and a CIE standard light source C were employed. Further, each of said standard materials was measured for its ASTM color by five measurers (A-E) by the use of a conventional ASTM chromometer.

The results so obtained by the above measurement are shown in Table 1 and FIG. 1.

TABLE 1

| Standard material No. | ASTM color | Mixing ratio of colorants | Dilution | Sum of optical densities $\Sigma D$ | ASTM color measured | | | | |
|---|---|---|---|---|---|---|---|---|---|
| | | | | | Measurer A | Measurer B | Measurer C | Measurer D | Measurer E |
| 1 | 1 | (1) | 100 | 0.87 | 1.0 | L1.0 | 1.0 | 1.0 | L1.0 |
| 2 | 3 | (2) | 19 | 3.17 | L3.0 | 3.0 | 3.0 | L3.0 | 3.0 |
| 3 | 5 | (3) | 10.3 | 5.20 | 5.0 | 5.0 | 5.0 | 5.0 | L5.0 |
| 4 | 7 | (4) | 5.9 | 6.82 | L7.0 | 7.0 | 7.0 | 7.0 | L7.0 |

As can be seen from Table 1 and FIG. 1, the sum ($\Sigma D$) of the optical densities of each of the standard materials corresponds appropriately to each ASTM color. Furthermore, the repetitive error of the $\Sigma D$ value was favorably small.

Therefore, by the use of the photoelectric colorimeter which was calibrated with the four kinds of standard materials mentioned above as to ASTM colors 1, 3, 5 and 7, time instrumental measurement of petroleum products for their ASTM color could be carried out quantitatively and accurately.

EXAMPLE 2

Dilute solutions of colorants (i)-(vii) obtained in the same manner as in Example 1 were mixed together in the mixing ratios by volume of:

(1) (i)210:(ii)26:(iii)0:(iv)13:(v) 0:(vi)2:(vii)3, and
(4) (i)183:(ii)53:(iii)13:(iv)11:(v)16:(vi)1:(vii)3, to obtain two kinds of mixed solutions. Subsequently, a predetermined amount of each of the two kinds of mixed solutions was diluted with n-$C_{12}$ to obtain two kinds of standard materials whose colors correspond respectively to ASTM colors 1 and 7.

The sum ($\Sigma D$) of optical densities of each of these standard materials was measured by the use of the same photoelectric colorimeter as used in Example 1. Further, each of said standard materials was measured for its ASTM color by 5 measurers (A-E) by the use of a conventional ASTM chromometer.

The results thus obtained were the same as those obtained in Example 1.

Therefore, even when there was used the photoelectric colorimeter which was calibrated with the two kinds of standard materials mentioned above as to ASTM colors 1 and 7, the instrumental measurement of petroleum products for their ASTM color could also be carried out quantitatively and accurately.

What is claimed is:

1. A set of standard materials, which comprises at least two kinds of standard materials, for calibration of a photoelectric colorimeter used for the instrumental measurement of petroleum products for their ASTM color, comprising at least two kinds of standard materials each of which is a mixed solution having a color corresponding to an ASTM color and comprises (a) at least five colorants selected from the group consisting of (i) 3-methyl-1-phenyl-4-(phenylazo)-pyrazol-5-ol, (ii) 1-(phenylazo)-2-naphthalenol, (iii) 1-[[4-[(dimethylphenyl)azo]dimethylphenyl]azo]-2-naphthalenol, (iv) 1,5(or 1,8)-bis[(4-methylphenyl)amino]-9,10-anthracenedione, (v) 1-hydroxy-4-[(4methylphenyl)amino]-9,10-anthracenedione, (vi) 1,4-bis(butylamino)-9,10-anthracenedione and (vii) 1,4bis[(4-butylphenyl)amino]-5,8-dihydroxy-9,10-anthracenedione, (b) 1-phenyl-1-xylylethane as a solvent for said colorants, and (c) dodecane as a diluent for the resulting solution;

said colorants (i)-(vii) being mixed together in a ratio by volume selected from the group consisting of
(1) (i)210:(ii)26:(iii)0:(iv)13:(v) 0:(vi)2:(vii)3,
(2) (i)200:(ii)29:(iii)7:(iv)6:(v) 4:(vi)2:(vii)4,
(3) (i)200:(ii)58:(iii)10:(iv)16:(v) 8:(vi)0:(vii)8, and
(4) (i)183:(ii)53:(iii)13:(iv)11:(v)16:(vi)1:(vii)3.

2. A method for instrumental measurement of petroleum products for their ASTM color by a photoelectric colorimeter, which comprises calibrating the photoelectric colorimeter by the use of at least two kinds of standard materials each of which is a mixed solution having a color corresponding to an ASTM color and comprises (a) at least five colorants selected from the group consisting of (i) 3-methyl-1-phenyl-4-(phenylazo)-pyrazol-5-ol, (phenylazo)-pyrazol-5-ol, (ii) 1-(phenylazo)-2naphthalenol, (iii) 1-[[4-[(dimethylphenyl)azo]dimethylphenyl]azo]-2-naphthalenol, (iv) 1,5(or 1,8)-bis[(4-methylphenyl) amino]-9,10-anthracenedione, (v) 1-hydroxy-4-[(4methylphenyl)amino]-9,10-anthracenedione, (vi) 1,4-bis(butylamino)-9,10-anthracenedione and (vii) 1,4bis[(4-butylphenyl)amino]-5.8-dihydroxy-9,10-anthracenedione, (b) 1-phenyl-1-xylylethane as a solvent for said colorants, and (c) dodecane as a diluent for the resulting solution;

said colorants (i)-(vii) being mixed together in a ratio by volume selected from the group consisting of
(1) (i)210:(ii)26:(iii)0:(iv)13:(v) 0:(vi)2:(vii)3,
(2) (i)200:(ii)29:(iii)7:(iv)6:(v) 4:(vi)2:(vii)4,
(3) (i)200:(ii)58:(iii)10:(iv)16:(v) 8:(vi)0:(vii)8, and
(4) (i)183:(ii)53:(iii)13:(iv)11:(v)16:(vi)1:(vii)3.

* * * * *